United States Patent [19]
Strike et al.

[11] 3,979,446
[45] Sept. 7, 1976

[54] PROSTAGLANDIN INTERMEDIATE

[75] Inventors: Donald P. Strike, St. Davids; Wenling Kao, Devon; Richard L. Fenichel, Wyncote, all of Pa.

[73] Assignee: American Home Products Corporation, New York, N.Y.

[22] Filed: Apr. 11, 1975

[21] Appl. No.: 567,449

Related U.S. Application Data

[62] Division of Ser. No. 446,835, Feb. 28, 1974, Pat. No. 3,919,302.

[52] U.S. Cl. ............................................. 260/514 D
[51] Int. Cl.$^2$ ...................................... C07C 177/00
[58] Field of Search .......................... 260/514 D, 408

[56] References Cited
OTHER PUBLICATIONS
Crabbe et al., Chem. & Ind., p. 635 (1973).

*Primary Examiner*—Robert Gerstl
*Attorney, Agent, or Firm*—David E. Frankhouser

[57] ABSTRACT

The topical application of 7-(5α-hydroxy-2β-[(3RS)-3-hydroxy-3-methyl-trans-1-octenyl]-3α-methyl-1α-cyclopentyl)-cis-5-heptenoic acid, 7-(5α-hydroxy-2β-[(3RS)-3-hydroxy-3-methyl-trans-1-octenyl]-1α-cyclopentyl)-cis-5-heptenoic acid, or 7-(2β-[(3RS)-hydroxy-3-methyl-trans-1-octenyl]-5-oxo-1α-cyclopentyl)-cis-5-heptenoic acid to a wound surface can be employed to attenuate bleeding. The compounds are prepared from the prostaglandin PGA$_2$.

1 Claim, No Drawings

PROSTAGLANDIN INTERMEDIATE

This is a division of application Ser. No. 446,835, filed Feb. 28, 1974, now U.S. Pat. No. 3,919,302.

BACKGROUND OF THE INVENTION

The control of bleeding during surgery is of considerable importance for the prevention of blood loss and the maintenance of a clear surgical field. For the prevention of gross bleeding from an exposed severed large artery or vein, where there is considerable intravasculr pressure, mechanical means, such as pressure or clamping, or cauterization are employed. For the control of bleeding from small blood vessels, where intravascular pressure does not prevent clotting, various methods may be used. One method comprises the topical application of thrombin to the wound surface whereby clotting is promoted by direct action of the thrombin of fibrinogen. Other methods employ substances which arrest bleeding by providing a mechanical matrix that facilitates clotting. Various absorbable substances used for this purpose are absorbable gelatin sponge (Gelfoam); oxidized cellulose (oxycel), or fibrin foam. A combination of such substances with thrombin (e.g. by saturating a pad of the absorbable substance with a thrombin solution) is especially effective.

The present invention provides an improved method for the attenuation of bleeding at a wound surface. The method comprises the topical application to the wound surface of an effective amount of prostaglandin derivative selected from the group consisting of:

a. 7-(5α-hydroxy-2β-[(3RS)-3-hydroxy-3-methyl-trans-1-octenyl]-3α-methyl-1α-cyclopentyl)cis -5-heptenoic acid;

b. 7-(5α-hydroxy-2β-[(3RS)-classes: -hydroxy-3-methyl-trans-1-octenyl ]-1α-cyclopentyl)-cis-5-heptenoic acid; and c. 7-(2β-[(3RS)-hydroxy-3-methyl-trans-1-octenyl]-5-oxo-1α-cyclopentyl)-cis-5-heptenoic acid.

The invention also contemplates the novel chemical compound:

7-(5α-hydroxy-2β-[(3RS)-3-hydroxy-3-methyl-trans-1-octenyl]-3α-methyl-1α-cyclopentyl)-cis-5-heptenoic acid.

Said compound is useful in the method hereinabove described.

Also contemplated by this invention is the chemical compound 7-[5α-hydroxy-3α-methyl-2β-(3-oxo-trans-1-octenyl)-1α-cyclopentyl]-cis-5-heptenoic acid, which is useful as an intermediate for preparing 7-(5α-hydroxy-2β-[(3RS)-3-hydroxy-3-methyl-trans-1-octenyl]-3-α-methyl-1α-cyclopentyl)-cis-5-heptenoic acid.

It is believed that the capacity of the compounds above-described to arrest bleeding is a consequence of their ability to promote platelet aggregation which is the initial step of the clotting process and is necessary for releasing platelet factors that act to convert prothrombin to thrombin. The method of the invention therefore, offers advantages in that the attenuation of bleeding is accomplished by a physiological process which avoids mechanical means and the introduction into the wound of a foreign protein (thrombin). It will be appreciated that the method is less effective in controlling bleeding from larger blood vessels where intravascular pressure might prevent clot formation. The method is especially useful to control bleeding from capillaries or small veins.

In practicing the method of the invention, the particular compound employed for the control of bleeding can be applied topically to the wound surface in a number of ways. The compound can be dissolved in a pharmacologically acceptable, non-toxic, aqueous sterile solution (such as physiological saline or physiological saline buffered to pH 7.4). The solution can be applied by irrigation or spraying. For such purposes, a syringe or an aerosol spray can be employed. Further, the compound, dissolved in a sterile solution, can be applied to a pad of an absorbable substance (absorbable gelatin sponge, oxidized cellulose, or fibrin foam) which is then placed on the wound surface. The pad acts as a preformed network to trap the blood, and it can be kept in place after closure of the wound since the pad is completely absorbed in 4 to 6 weeks.

When the compounds are applied dissolved in an aqueous solution, the active ingredient can be present at a concentration of from about 50 to about 1000 μg/ml. A concentration of from about 200 to about 500 μg/ml is preferred.

The amount of compound required to effect attenuation of bleeding will vary with the size of the wound surface, the source of the bleeding, and the severity of the bleeding. In general, the compound is applied in small incremental amounts until the desired attenuation is achieved.

The compounds utilized in the method of this invention are prepared from the known starting materials $PGA_2$ or 15-epi-$PGA_2$. 15-epi-$PGA_2$ can be obtained from the coral *Plexaura homomalla* by a procedure as described by A. Weinheimer and R. Spraggins in *Tetrahedron Letters*, 59, 5185 (1969), and $PGA_2$ can be prepared from 15-epi-$PGA_2$ by an epimerization procedure as described by Bundy et al. in *Ann. of the New York Acad. of Sci.*, 180, 76 (1971). 7-(5α-Hydroxy-2β-[(3RS)-3-hydroxy-3-methyl-trans-1-oxtenyl]-1α-cyclopentyl)-cis-5-heptenoic acid and 7(2β-[(3RS)-3-hydroxy-3-methyl-trans-1-octenyl]-5-oxo-1α-cyclopentyl)- cis-5-heptenoic acid are described in U.S. Patent Application Ser. No. 383,007, filed July 26, 1973. The preparation of the compounds employed in the method of this invention from readily available starting materials is described below in Examples I to VIII.

EXAMPLE I 7-(5α-Hydroxy-2β-[(3R)-3-Hydroxy-Trans-1-Octenyl]-1α-Cyclopentyl) -Cis-5-Heptenoic Acid and 7-(5β-Hydroxy-2β-[(3R)-3-Hydroxy-Trans-1-Octenyl]-1α-Cyclopentyl) -Cis-5-Heptenoic Acid An ice-cooled solution of 4.0 g. of 7-(2β-[(3R)-3-hydroxy -trans-1-octenyl]-5-oxo-1α-cyclopent-3-enyl)-cis-5-heptenoic acid (15-epi-$PGA_2$) in 110 ml. of a 10:1 mixture methanol water is treated with 2.2 g. of sodium borohydride, and stirred at 25° for 7 hours. The mixture is concentrated under vacuum at 40°, the residue diluted with water, acidified with acetic acid and the mixture partitioned with ether. After washing and drying, the extract is evaporated and the residue chromatographed on silica. Elution with 35% ethyl acetate-hexane affords the first title product as an oil, $\lambda_{max}^{film}$ 2.95, 3.4, 5.8, 7.1, 8.1, 8.8, 9.7, 10.3 μ. NMR: δ 5.48

(M, 4, olefinic H), 4.62 (2, OH), 4.28 (M 2, 9 and 15-H) ppm. Mass spectrum M$^+$ at m/e 338 (theory 338), M$^+$ -H$_2$O at m/e 320.2331 (theory 320.2350).

Further elution with 40% ethyl acetate-hexane gives the second title product as an oil, $\lambda_{max}^{film}$ 3.0, 3.4, 5.8, 7.1, 8.1, 9.35, 10.3 μ. NMR: δ 5.55 (M, 4, olefinic H), 4.58 (s, OH), 4.05 (M, 2, 9 and 15-H) ppm. Mass spectrum: M$^+$ at m/e 338 (theory 338). M$^+$ -H$_2$O at m/e 320.2384 (theory 320.2350).

EXAMPLE II

7-[5α-Hydroxy-2β-(3-Oxo-Trans-1-Octenyl)-1α-Cyclopentyl]-Cis-5-Heptenoic Acid A solution of 3.63 g. of 7-(5α-hydroxy-2β-[(3R-3-hydroxy-trans-1-octenyl]-1α-cyclopentyl)-cis-5-heptenoic acid in 250 ml. of dioxane is treated with 3.63 g. of 2,3-dichloro-5,6-dicyano-1,4-benzoquinone and stirred at 55° for 40 hours under nitrogen. The solution is concentrated under vacuum at 40° and the residue chromatographed on silica. Elution with 30% ethyl acetate-hexane yields 1.8 g. of the title product as an oil, $\lambda_{max}^{film}$ 3.0 (shoulder), 3.4, 5.8, 6.0 (shoulder), 6.15 (shoulder), 7.1, 8.1, 10.2 μ. UV: $\lambda_{max}^{EtOH}$ 232 mμ (ε 12,000). NMR: δ 6.72 (dd, 1, J=5.3 and 15, 13-H), 6.08 (d, 1, J=15, 14-H), 5.40 (M, 2, 5, and 6-H), 4.25 (M, 1, 9-H) ppm. Mass spectrum: QM$^+$ at m/e 337 (theory 337), QM$^+$ -H$_2$O at m/e 319 (theory 319).

EXAMPLE III

7-(5α-Hydroxy-2β-[(3RS)-3-Hydroxy-3-Methyl-Trans-1-Octenyl]-1α-Cyclopentyl)-Cis-5-Heptenoic Acid An ice-cooled solution of 1.7 g. of 7-[5α-hydroxy-2β-(3-oxo-trans-1-octenyl) -1α-cyclopentyl]-cis-5-heptenoic acid in 150 ml. of tetrahydrofuran is treated with 15 ml. of 3M methyl magnesium bromide in ether dropwise over 10 minutes under nitrogen. After stirring at 0° for 45 minutes, the mixture is added to ammonium chloride solution, acidified with acetic acid and extracted with ether. After washing and drying, the extract is evaporated and the residue chromatographed on silica. Elution with 35% ethyl acetate-hexane affords 1.07 g. of the title product as an oil, $\lambda_{max}^{film}$ 3.0, 3.4, 5.8, 8.1, 10.3 μ. NMR: δ 5.42 (M, 4, olefinic H), 5.12 (s, 3, OH), 4.20 (M, 1 9H), 1.28 (s, 15-CH$_3$) ppm. Mass spectrum: QM$^+$-H$_2$O at m/e 335 (theory 335).

EXAMPLE IV

7-(2β-[(3RS)-3-Hydroxy-3-Methyl-Trans-1-Octenyl]-5-Oxo-1α-Cyclopentyl) -Cis-5-Heptenoic Acid An ice-cooled solution of 1.02 g. of 7-(5α-hydroxy-2β-[(3RS)-3-hydroxy-3-methyl-trans-1-octenyl]-1α-cyclopentyl)-cis-5-heptenoic acid in 80 ml. of acetone is treated dropwise with Jones reagent until the orange color persists. After stirring at 0° for ½ hour, the mixture is treated with 5 ml. of methanol and dilute sodium bicarbonte until basic. The mixture is diluted with water, acidified with acetic acid and extracted with ether. After washing and drying, the extract is evaporated and the residue chromatographed on silica. Elution with 30% ethyl acetate-hexane give 0.12 g. of the title product as an oil, $\lambda_{max}^{film}$ 3.0, 3.4, 5.75, 7.1, 8.15, 8.65, 10.3 μ. NMR: δ 6.80 (s, 2, OH), 5.72 (M, 2, 13 and 14-H), 5.52 (M, 2, 5 and 6-H), 1.30 (s, 15-CH$_3$) ppm. Mass spectrum: QM$^+$ at m/e 351 (theory 351).

EXAMPLE V

7-[2β-[(3S)-powder -Hydroxy-Trans-1-Octenyl]-3α-methyl-5-Oxo-1α-Cyclopentyl]-Cis-5-Heptenoic Acid and 7-[2β-[(1 S)-3-Hydroxy-Trans-11 -3β-Methyl-5-Oxo-1α-cyclopentyl] -Cis-5-Heptenoic Acid A solution of 3.0 g. of PGA$_2$ in 60 ml. of THF is added dropwise to an ice-cooled mixture of 24 ml. of 3M methyl magnesium bromide and 5.0 g. of cuprous chloride in 120 ml. of THF and stirred at 0°C for 1 hour. The mixture is added to aqueous ammonium chloride solution and extracted with ether. After washing with water and drying over magnesium sulfate, the extract is concentrated to give crystalline material. Filtration followed by recrystallization from ether-pentane affords 1.2 g. of the first title product, m.p. 68°–70°C; $\lambda_{max}^{KBr}$ 3.0 (shoulder), 3.5, 5.8, 6.9, 7.6, 8.05, 8.55, 10.3 μ; NMR: δ 6.93 (s, 2, OH), 5.54 (m, 13 and 14-H), 5.38 (m, 5 and 6-H), 4.16 (m, 1, 15-H); Mass spectrum: M$^+$ at m/e 350.2476 (theory 350.2455).

Evaporation of the filtrates and silica chromatography of the residue with 30% ethylacetate in hexane followed by crystallization from ether-pentane gives 0.09 g. of the second title product, m.p. 72°–74°C; UV: $\lambda_{max}^{film}$ 3.0 (shoulder), 3.5, 5.8 (shoulder), 5.9, 7.0, 8.15, 8.45, 10.4 μ; NMR: δ 7.05–6.22 (m, 2, OH), 5.48 (m, 4, olefinic), 4.15 (m, 1, 15-H) ppm; Mass spectrum: M$^+$ at m/e 350.2460 (theory 350.2455).

EXAMPLE VI

7-(5α-Hydroxy-2β-[(3S)-3-Hydroxy-Trans-1-Octenyl]-3α-methyl-1α-cyclopentyl)-Cis-5-Heptenoic Acid and 7-(5β-Hydroxy-2β-[(3S)-3-Hydroxy-Trans-1-Octenyl]-3α-methyl-1α-cyclopentyl) -Cis-5-Heptenoic Acid An ice-cooled solution of 7.8 g. of 7-(2β-[(3S)-3-hydroxy-trans-1-octenyl]-3α-methyl-5-oxo-1α-cyclopentyl)-cis-5-heptenoic acid in 150 ml. of methanol is treated with 3.5 g. of sodium borohydride and stirred at 0°C for 2 hours. The mixture is diluted with water and acidified with acetic acid. Extraction of the resulting mixture with ether, followed by washing, drying and evaporation of the extract gives the crude product. Silica chromatography with 30 % ethyl acetate in hexane affords 3.5 g. of the first title product as an oil; $\lambda_{max}^{film}$ 3.0, 3.5, 5.85, 6.9, 7.15, 8.1, 8.9, 9.8, 10.35 μ; NMR: δ 5.57 (s, 3, OH), 6.0–5.17 (m, 4, olefinic), 4.21 (m, 2, 9 and 15-H), 1.01 (d, J=4.5, 11-methyl) ppm; Mass spectrum: M$^+$ at m/e 352.2670 (theory 352.2613). Further elution with 30% ethyl acetate in hexane affords 3.0 g. of the second title product as an oil; UV: $\lambda_{max}^{film}$ 3.0, 3.5, 5.85, 6.9, 7.15, 8.2, 10.4 μ; NMR:δ 5.61 (s, 3, OH), 5.52 (s, 4, olefinic), 4.10 (m, 2, 9 and 15-H), 0.91 (d, J=4.5, 11-methyl) ppm; Mass spectrum: M$^+$ at m/e 352 (theory 352), M$^+$-H$_2$O at m/e 334.2564 (theory 334.2507).

EXAMPLE VII

7-[5α-Hydroxy-3α-methyl-2β-(3-Oxo-Trans-1-Octenyl)-1αCyclopentyl]-Cis-5-Heptenoic Acid

A solution of 3.3 g. of 7-(5α-hydroxy-2β-[(3S)-3-hydroxy-trans-1-octenyl]-3α-methyl-1α-cyclopentyl)-cis-3-heptenoic acid and 3.0 g. of 2,3-dichloro-5,6-dicyano-1,4-benzoquinone in 100 ml. of dioxane is stirred at 55°C for 22 hours. After filtering, the solution is evaporated and the residue chromatographed on silica. Elution with 25% ethyl acetate in hexane affords 2.9 g. of the title product as an oil; $\lambda_{max}^{film}$ 3.0 (shoulder), 3.5, 5.85, 6.0, 6.2, 6.9, 8.2 (broad), 10.25 $\mu$; UV: $\mu_{max}^{EtOH}$ 233 m$\mu$ ($\epsilon$ 14,000); NMR: $\delta$ 6.75 (dd, J=16, 7.5, 13-H), 6.32 (s, 2, OH), 6.19 (d, J=16, 14H), 5.48 (m 2, 5 and 6-H), 4.32 (m, 1, 9H) ppm; Mass spectrum: M$^+$ at m/e 350.2499 (theory 350.2455).

EXAMPLE VIII

7-(5α-Hydroxy-2β[(3RS)-3-Hydroxy-3-Methyl-Trans-1-Octenyl]-3α-Methyl-1α-Cyclopentyl)-Cis-5-Heptenoic Acid

An ice-cooled solution of 1.0 g. of 7-[5α-hydroxy-3α-methyl-2β-(3-oxo-trans-1-octenyl) -1α-cyclopentyl]-cis-5-heptenoic acid in 50 ml. of THF is treated with 8 ml. of 3M methyl magnesium bromide and stirred at 0°C for 2 hours. The mixture is added to aqueous ammonium chloride solution and extracted with ether. After washing with water and drying over magnesium sulfate, the extract is evaporated and the residue chromatographed on silica. Elution with 25% ethyl acetate in hexane affords the title product as an oil, UV: $\lambda_{max}^{film}$ 3.0, 3.5, 5.85, 6.9, 8.95, 9.75, 10.33 $\mu$; NMR: $\delta$ 5.8–5.2 (m, 4, olefinic). 5.43 (s, 3, OH), 4.30 (m, 1, 11-H), 1.30 (s, 15-methyl), 1.0 (d, J=5, 11-methyl) ppm; Mass spectrum: M$^+$-H$_2$O at m/e 348.2682 (theory 348.2664).

EXAMPLE IX

Rats are anesthetized and the skin and connective tissue cut through so that a vein is exposed. A standardized nick of the vein 1 to 2 mm. deep is made by a lancet to yield a free flow of blood. Into the bleeding surface is dripped (one drop every 5–6 seconds) a solution of the compound dissolved in physiological saline. The time required (in seconds) for bleeding is measured. A control group of rats are treated similarly with a physiological saline solution which does not contain the test compound. A significant decrease in bleeding time indicates activity.

Using 7-(2β-[(3RS)-3-hydroxy-3-methyl-trans-1-octenyl]-5-oxo-1α-cyclopentyl)-cis-5-heptenoic acid dissolved in physiological saline at a concentration of 200 $\mu$g/ml., the following results are obtained:

|  | No. of Animals | Bleeding Time (sec.) ± Standard Error |
|---|---|---|
| Control | 10 | 97.4 ± 6.2 |
| 7-(2β-[(3RS)-3-hydroxy-3-methyl-trans-1-octenyl]-5-oxo-1α-cyclopentyl)-cis-5-heptenoic acid. | 10 | 77.8 ± 5.6 |

Significance: <0.05

EXAMPLE X

Rats are anesthetized and the abdominal cavity is opened so that a portion of the large intestine is exposed to show an extensive matrix of small blood vessels. A 1–2 cm. superficial cut across the vessels is made with a scalpel. Into the wound is dripped a solution of the test compound dissolved in physiological saline. The time required (in seconds) for bleeding to stop is measured. A control group of rats are treated similarly with a physiological saline solution which does not contain the test compound. A significant decrease in bleeding time indicates activity.

Using 7-(2β-[(3RS)-3-hydroxy-3-methyl-trans-1-octenyl]-5-oxo-1α-cyclopentyl) -cis-5-heptenoic acid dissolved in physiological saline at a known, of 400 $\mu$g/ml., the following results are obtained:

|  | No. of Animals | Bleeding Time (sec.) ± Standard Error |
|---|---|---|
| Control | 6 | 395 ± 25 |
| 7-(2β-[(3RS)-3-hydroxy-3-methyl-trans-1-octenyl]-5-oxo-1α-cyclopentyl)-cis-5-heptenoic acid. | 7 | 174 ± 16.9 |

Significance: <0.001

EXAMPLE XI

Fasted male rats are given an injection (IV) into the leg vein of the test compound dissolved in physiological saline. Blood is obtained by cardiac puncture at intervals after the injection. Whole blood clotting times (Lee White) are determined A control group of rats are similarly treated by injection with physiological saline which does not contain the test compound. The results are shown below:

TABLE I

| Compound | Dose ($\mu$g/kg) | No. of Rats | 1 min. | No. of Rats | 5 min. | Significance |
|---|---|---|---|---|---|---|
| Control | — | 8 | 341.2 ± 13.1 | 7 | 340.7 ± 13.6 |  |
| A | 250 | 11 | 330.0 ± 22.9 | 9 | 296.7 ± 18.5 | N.S. (1 min. and 5 min.) |
| Control | — | 9 | 378.3 ± 12.4 | 8 | 356.3 ± 25.1 |  |
| A | 500 | 9 | 281.7 ± 12.4 | 7 | 242.1 ± 24.9 | <0.01 (1 min. and 5 min.) |
| Control | — | 9 | 393 ± 10.9 | 8 | 401 ± 8.4 |  |
| B | 500 | 11 | 358 ± 10.9 | 8 | 363 ± 9.0 | <0.05 (1 min. and 5 min.) |
| Control | — | 10 | 405.0 ± 21.1 | 8 | 373.1 ± 24.9 |  |
| B | 250 | 10 | 363.8 ± 14.2 | 5 | 369.0 ± 22.2 | N.S. (1 min. and 5 min |
| Control | — | 8 | 433.1 ± 9.8 | 5 | 435.0 ± 9.2 |  |

TABLE I-continued

| | | | Mean Lee White Clotting Time (Sec. ± Standard Error) | | | |
|---|---|---|---|---|---|---|
| Compound | Dose (μg/kg) | No. of Rats | 1 min. | No. of Rats | 5 min. | Significance |
| C | 500 | 8 | 405.0 ± 12.5 | 6 | 412.5 ± 16.3 | N.S. (1 min. and 5 min.) |

N.S. = Not significant
KEY TO COMPOUNDS TESTED
Compound A: 7-(2β-[(3RS)-3-hydroxy-3-methyl-trans-1-octenyl]-5-oxo-1α-cyclopentyl)-cis-5-heptenoic acid
Compound B: 7-(5α-hydroxy-2β-[(3RS)-3-hydroxy-3-methyl-trans-1-octenyl]-1α-cyclopentyl)-cis-5-heptenoic acid
Compound C: 7-(5α-hydroxy-2β-[(3RS)-3-hydroxy-3-methyl-trans-1-octenyl]-3α-methyl-1α-cyclopentyl)-cis-5-heptenoic acid

EXAMPLE XII

Human whole blood (containing 3.8% sodium citrate) is centrifuged at about 422 G for 3 minutes at 5°C in a Sorvall Centrifuge (or equivalent) to separate the red blood cells from the platelet rich plasma (PRP). The supernatant PRP is separated and the remainder is centrifuged at 1200 G for 12 minutes to obtain a platelet poor plasma for dilution and standardization of the instrument. In an automated Payton aggregometer, a cell containing 1.0 ml. of PRP is stirred at 1,100 RPM, and the compound to be tested is added dissolved in 0.2 ml. of buffered saline to give a concentration of 1–10 μg/ml. The curve of percent light transmission at 610 mμ is followed for six minutes. Active compounds exhibit a significant increase in light transmission over a control run without the addition of the test compound. A standard is also run using adenosine diphosphate (ADP) as the agent added to PRP for inducing platelet aggregation. Using the change in light transmissions obtained with the test compound as compared to the change obtained with ADP, the platelet aggregating activity of the test compounds can be expressed in terms of their equivalency to ADP, which is a potent aggregating agent. The concentrations of the test compounds calculated to be equivalent to ADP for inducing aggregation are given in the following table:

| Compound | Concentration (μM) | Equivalent to ADP, (μM) * |
|---|---|---|
| A | 13.5 | 7.2; 4.2 (Mean: 5.7) |
| A | 8.1 | 6.8; 3.7 (Mean: 5.3) |
| B | 13 | 8.0; 5.6 (Mean: 6.8) |
| B | 7.8 | 6.3 |
| C | 13 | 5.2 |
| C | 7.8 | 2.2; 5.1 (Mean: 3.7) |

* Mean values calculated from 2 values. Otherwise, single values are given
Key to Compounds Tested
Compound A: 7-(2β-[(3RS)-3-hydroxy-3-methyl-trans-1-octenyl]-5-oxo-1α-cyclopentyl)-cis-5-heptenoic acid
Compound B: 7-[5α-hydroxy-2β-[(3RS)-3-hydroxy-3-methyl-trans-1-octenyl]-1α-cyclopentyl)-cis-5-heptenoic acid
Compound C: 7-(5α-hydroxy-2β-[(3RS)-3-hydroxy-3-methyl-trans-1-octenyl]-3α-methyl-1α-cyclopentyl)-cis-5-heptenoic acid Platelet aggregation is the initial step in the blood clotting process and is necessary for the release of factors from the platelets which act to convert prothrombin to thrombin. Agents which promote platelet aggregation, therefore would be expected to promote clotting and the platelet aggregation test, described above, is useful for predicting in vivo clotting activity.

What is claimed is:
1. The compound which is 7-[5α-hydroxy-3α-methyl-2β-(3-oxo-trans-1-octenyl) -1α-cyclopentyl]-cis-5-heptenoic acid.

* * * * *